United States Patent
Gilman

(10) Patent No.: US 6,787,682 B2
(45) Date of Patent: Sep. 7, 2004

(54) ABSORBENT FOAM WOUND DRESSING

(75) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 127 days.

(21) Appl. No.: 10/007,445

(22) Filed: Nov. 5, 2001

(65) Prior Publication Data

US 2003/0088202 A1 May 8, 2003

(51) Int. Cl.[7] .................................................. A61F 13/00
(52) U.S. Cl. ............................. 602/58; 602/42; 602/43; 602/46; 602/54
(58) Field of Search ................. 602/41–59; 128/888, 128/889; 604/304–308; 424/443–449

(56) References Cited

U.S. PATENT DOCUMENTS

| | | | |
|---|---|---|---|
| 3,903,232 A | 9/1975 | Wood et al. ................. 264/157 |
| 4,339,550 A | 7/1982 | Palinczar et al. ............. 521/99 |
| 4,907,579 A | 3/1990 | Kum ........................... 128/156 |
| 5,056,510 A | 10/1991 | Gilman ........................ 128/155 |
| 5,064,613 A | 11/1991 | Higgs et al. .................. 422/16 |
| 5,086,764 A | 2/1992 | Gilman ........................ 602/42 |
| 5,106,362 A | 4/1992 | Gilman ........................ 602/47 |
| 5,244,457 A | 9/1993 | Karami et al. ................ 602/55 |
| 5,409,472 A | 4/1995 | Rawlings et al. ........... 604/307 |
| 5,556,375 A | * 9/1996 | Ewall ........................... 602/58 |
| 5,603,946 A | 2/1997 | Constantine ................ 424/445 |
| 5,902,260 A | * 5/1999 | Gilman et al. ................ 602/57 |

FOREIGN PATENT DOCUMENTS

| WO | WO 94/21207 | 9/1994 |
| WO | WO 97/11658 | 4/1997 |
| WO | WO 02/05737 | 1/2002 |
| WO | WO 04/05737 | 1/2002 |

* cited by examiner

Primary Examiner—Kim M. Lewis
(74) Attorney, Agent, or Firm—Marshall, Gerstein & Borun LLP

(57) ABSTRACT

A highly conformable and absorbent polymeric foam wound dressing is disclosed, such dressing being particularly useful in preventing pooling of fluid in a draining wound while at the same time maintaining surrounding skin surfaces in a relatively dry state.

8 Claims, 1 Drawing Sheet

US 6,787,682 B2

ABSORBENT FOAM WOUND DRESSING

BACKGROUND AND SUMMARY OF THE INVENTION

U.S. Pat. No. 5,086,764 discloses various forms of wound dressings in which an absorbent fabric 12 is located either in a wound cavity beneath a base sheet 14 or directly above an aperture 18 in that base sheet. In either case, the absorbent fabric 12 is removable or separable from the base sheet 14 so that it may be easily changed without disturbing that sheet when the fabric becomes saturated. In some versions, a back sheet 38 extends over the absorbent fabric and is secured thereto by a pressure-sensitive coating 40.

Soft, compressible, highly absorbent and hydrophilic foams are also known for medical and dental use as disclosed, for example, in U.S. Pat. No. 3,903,232. While such foams may be of different polymeric compositions, the polyurethane foams disclosed in the aforementioned patent are exceptionally soft and hydrophilic, expanding quickly as they absorb aqueous fluids.

Other U.S. patents illustrating the state of the art are U.S. Pat. Nos. 5,146,362, 5,603,946, 5,244,457, 4,907,570, and 5,056,510.

A main aspect of the present invention lies in providing an improved wound dressing for preventing pooling of liquid in a draining or exuding wound while at the same time protecting the wound against contamination and maintaining the surrounding skin surfaces in a relatively dry state. The dressing utilizes a soft, hydrophilic polymeric foam layer that readily expands into a wound cavity as it absorbs wound exudate.

In the dressing of this invention, the absorbent foam layer is permanently secured to the backside of an elastomeric base film. The base film is vapor-permeable but liquid impermeable except for one or more generally central openings through which a portion of the underside of the foam layer is exposed. A pressure-sensitive adhesive coats the underside or bodyside surface of the film for securing the dressing to body surfaces at a wound site. The adhesive coating (or each such coating) of the base film is discontinuous or micro-porous so that it does not block the transmission of moisture vapor through the film.

An elastomeric backing layer extends over the back surface of the foam layer but ideally is not directly attached or adhered to the foam layer. The lack of adherence or attachment is important because it enhances conformability of the dressing to anatomical contours, and to changes in such contours as a patient moves about, and allows limited displacement of the foam layer away from the backing layer and expansion into a wound cavity when the dressing is in use. If desired, the outermost surface of the elastomeric backing layer may be covered by a soft foraminous foam layer having a multiplicity of wide openings, preferably taking the form of a stretchable foam grid, to assist in the handling, delivery, and application of the dressing at a wound site.

Other features, advantages and objects of the invention will become apparent from the specification and drawings.

DRAWINGS

DETAILED DESCRIPTION OF PREFERRED EMBODIMENT

Figure 1:
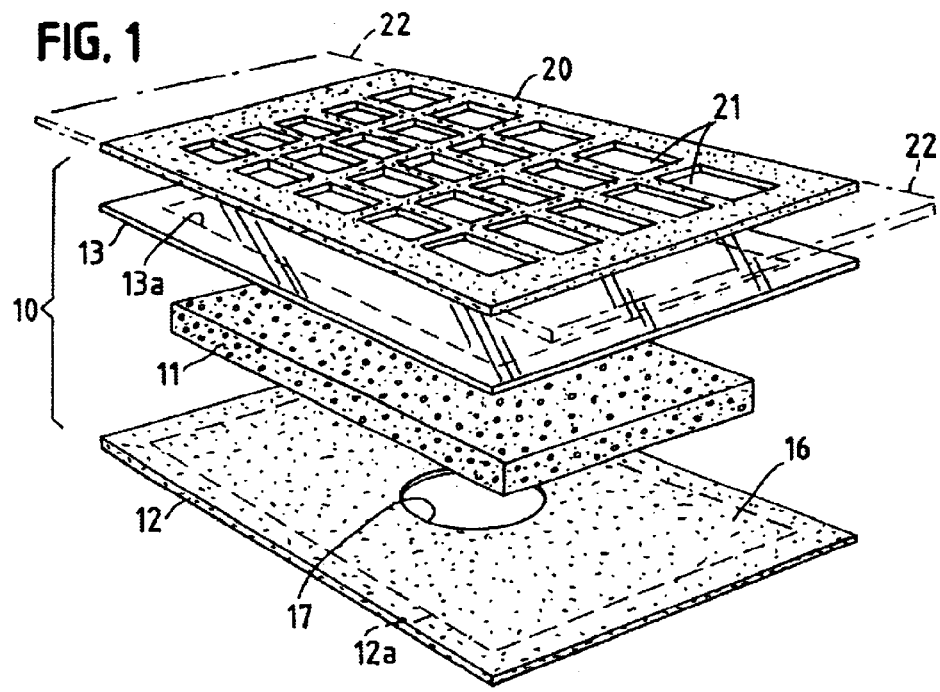
FIG. 1 is an exploded perspective view of a wound dressing embodying this invention.

Polymeric foams that are soft, exceptionally hydrophilic, and readily expandable as they absorb aqueous fluids are known in the art, one such foam being a polyurethane foam disclosed in aforementioned patent U.S. Pat. No. 3,903,232. Such a foam is prepared with polyoxyethylene, polyisocyanates, water and certain surfactants and has an exceptionally fine, uniform, soft, hydrophilic cell structure. The foam is of low density and may be characterized as being of open cell or semi-open cell in structure. It has an extreme affinity for aqueous fluids, being able to absorb and retain many times its weight of such fluids and characteristically swelling or expanding as it does so. When used in a wound dressing, such an expandable hydrophilic foam has been found capable of absorbing a substantial volume of fluid from a draining or exuding wound to prevent the pooling of liquid while at the same time maintaining the wound bed in moist and protected condition.

While a polyurethane foam of the type so described is preferred, it is believed that other soft, highly-absorbent polymeric foam materials are known and may be used in the dressing of this invention. An example of one polyurethane foam found to be particularly effective is available from Rynel Ltd., Inc., Boothbay, Me. under the designation Foam HPFL00562.

Referring to the drawings, the numeral 10 generally designates a wound dressing having a soft, absorbent, compressible, hydrophilic foam layer 11, a base film 12, and a backing layer or film 13. Both the base film and backing film are elastomeric and vapor-transmissible as well as liquid-impermeable. More specifically, such elastomeric films should have moisture vapor transmission values approximating or exceeding those of healthy skin. In general, the MTVR for each film should be at least 250 cc per square meter per 24 hours. A polyurethane film having a thickness within the general range of 0.25 mil to 2.0 mil, preferably about 0.5 mil, has been found suitable for both the base film and backing film, but other elastomeric film materials having similar properties may be used. For example, a polyester block copolymer marketed under the trademark "Hytrel" by du Pont De Nemours, Wilmington, Del. is believed suitable for both the base film and backing film.

Base film 12 has its bodyside surface coated with a suitable hypoallergenic pressure-sensitive adhesive 14. A conventional medical-grade acrylic adhesive is suitable but other pressure-sensitive adhesives such as hydrocolloid and hydrogel adhesives might be used. Adhesive layer 14 should be vapor permeable by reason of diffusibility or because of discontinuity or microporosity, all as well known in the art. To protect the adhesive layer 14 prior to use of the dressing, such layer is covered by a removable release sheet 15 shown only in phantom in FIG. 2. Such release sheet may be formed of siliconized paper or any other suitable material.

Figure 2:
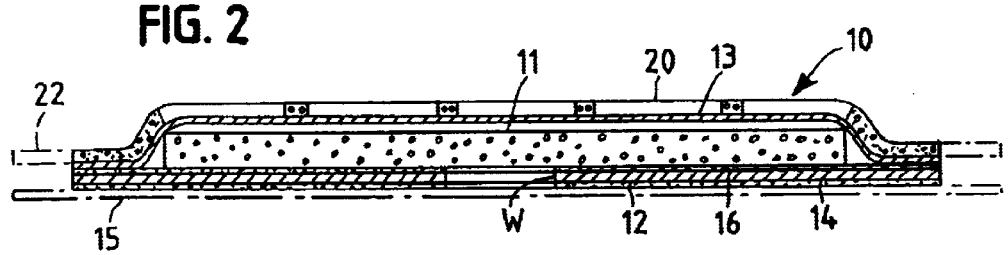
FIG. 2 is a schematic cross-sectional view of the dressing.

The back surface of base film 12 is permanently secured to the bodyside surface of foam layer 11, preferably by means of a vapor-permeable adhesive layer 16 which may be of the same composition as pressure-sensitive adhesive layer 14. It will be observed that foam layer 11 is smaller in outline than base film 12 and backing film 13 (which are of equal size) so that the borders of the respective films extend outwardly beyond the periphery of foam layer 11. In FIG. 1, broken lines 12a and 13a schematically delineate the border portions of the base and backing films that extend outwardly beyond the foam layer 11 and are secured to each other in such border area, preferably by means of the same adhesive layer 16 that secures foam 11 to base film 12. In a preferred embodiment of the invention, the upper or back surface of foam layer 11 is not adhered or otherwise secured directly to the bodyside surface of the backing layer 13. A spacing between the two is shown in FIG. 2 but such spacing is shown only for illustrative purposes and may not exist, at least until such time as the dressing is applied to a wound.

In the embodiment illustrated in the drawings, dressing 10 is shown to be generally rectangular in outline, but it is to be understood that such shape is not critical. It is important that the area of the dressing be substantially larger than that of the wound over which the dressing is applied so that the pressure-sensitive adhesive coating 14 sealingly engages the skin surfaces surrounding the wound over which the dressing extends. Instead of being rectangular in shape, the dressing may be generally circular or oval in outline or alternatively may be of any of a variety of selected shapes having areas substantially larger than the wound W to be covered.

Figure 3:
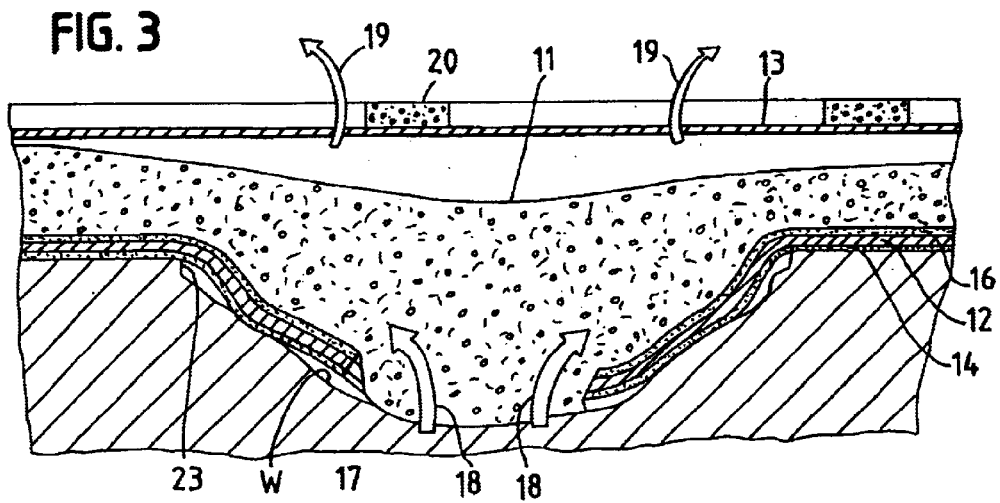
FIG. 3 is an enlarged fragmentary sectional view showing the dressing at a wound site.

Base film 12 with its pressure-sensitive adhesive coating 14 has at least one centrally-located opening 17 of a size smaller than that of the wound W over which the dressing extends. When the dressing is applied over a draining wound, the soft, deformable and highly absorbent foam layer 11 expands downwardly through opening 17 as it absorbs fluid from the wound cavity (as indicated by arrows 18 in FIG. 3). The elastomeric base film 12 is secured by pressure-sensitive adhesive layer 14 to the skin surfaces surrounding the wound W and, as shown in FIG. 3, that portion of the base film 12 surrounding opening 17 also extends downwardly into the wound about the edges 23 of the wound cavity. The base film thereby maintains the skin surface about the wound cavity in relatively dry condition and, in addition, directs liquid into that portion of the foam layer 11 disposed directly above base film 12 beyond the border of opening 17.

In a preferred embodiment in which the backing film 13 is free of attachment to the top surface of foam layer 11, the foam layer is free to expand downwardly into the wound cavity and away from elastomeric layer 13 as depicted in FIG. 3. The backing film thus presents no resistance to downward expansion of the foam. Moisture vapor may pass through backing film 13 as indicated by arrows 19, so that liquid absorbed by the foam layer 11 may convert to vapor form and pass through vapor-permeable backing layer 13.

In a preferred embodiment, dressing 10 is provided with an optional delivery-assisting layer 20 which takes the form of a soft, foraminous layer of stretchable polymeric foam extending over backing film 13. A multiplicity of wide apertures 21 are provided in layer 20 with such apertures preferably being of rectangular shape and giving layer 20 a grid-like appearance. The grid-portion of layer 20 may be secured by any suitable pressure-sensitive adhesive to the upper surface of elastomeric film 13.

As shown in FIGS. 1 and 2, layer 20 may be provided with opposite end portions 22 that project outwardly to function as tabs that be easily gripped by a user for purposes of holding and applying the dressing to a wound site. While a foam material as disclosed in U.S. Pat. No. 5,902,260 (the disclosure of which is incorporated by reference herein) is believed particularly suitable for layer 20, other materials, such as stretchable nonwoven polymeric materials, may instead be used. Further, layer 20, if used at all, may be weakly attached to backing film 13 by an adhesive that allows layer 20 to be peeled away from the backing film 13 after the dressing has been applied. In that connection, the outwardly-projecting tab portions 22 of the foam layer are also useful in gripping that layer and separating it from backing film 13.

While in the foregoing I have disclosed an embodiment of the invention in considerable detail for purposes of illustration, it will be understood by those skilled in the art that many of these details may be varied without departing from the spirit and scope of the invention.

What is claimed is:

1. A wound dressing comprising a foam layer of soft, hydrophilic polymeric foam having bodyside and backside surfaces; a base layer of elastomeric film adhered to said bodyside surface of said foam layer; said base layer having at least one generally centrally located opening therein exposing said foam layer through said opening; said base layer having a bodyside surface coated with a hypoallergenic pressure-sensitive adhesive for adhesively contacting wound and surrounding skin surfaces at a wound site; and a vapor-permeable liquid-impermeable elastomeric backing layer extending over said backside surface of said foam layer; said backing layer being unattached to said backside surface of said foam layer over said centrally located opening of said base layer.

2. The wound dressing of claim 1 in which said backing layer includes a peripheral edge portion secured to said base layer about said foam layer.

3. The wound dressing of claim 1 or 2 in which said foam layer is composed of a soft hydrophilic polyurethane foam.

4. The wound dressing of claim 1 or 2 in which said elastomeric film of said base layer is gas-permeable and liquid-impermeable.

5. The wound dressing of claim 1 or 2 in which a flexible and stretchable foraminous layer extends over the surface of said backing layer opposite from said foam layer.

6. The wound dressing of claim 5 in which said flexible foraminous layer is formed of soft, stretchable polymeric foam.

7. The wound dressing of claim 5 in which said foraminous layer has a multiplicity of openings of regular shape for viewing said backing layer therethrough.

8. The wound dressing of claim 7 in which said openings in said flexible foraminous layer are generally rectangular in shape and are arranged in a grid pattern.

* * * * *

UNITED STATES PATENT AND TRADEMARK OFFICE
CERTIFICATE OF CORRECTION

PATENT NO. : 6,787,682 B2
DATED : September 7, 2004
INVENTOR(S) : Thomas H. Gilman It is certified that error appears in the above-identified patent and that said Letters Patent is hereby corrected as shown below:

Column 4,
Lines 40, 43 and 46, "claim" should read -- claims --.

Signed and Sealed this

Fifteenth Day of February, 2005

JON W. DUDAS
*Director of the United States Patent and Trademark Office*